(12) United States Patent
Popek

(10) Patent No.: US 7,768,764 B2
(45) Date of Patent: Aug. 3, 2010

(54) ELECTROSTATIC DISCHARGE PROTECTION FOR MICROWAVE GUIDED WAVE STRUCTURE

(76) Inventor: Marc H. Popek, 9801 Bearpaw Ave., Las Vegas, NV (US) 89117

( * ) Notice: Subject to any disclaimer, the term of this patent is extended or adjusted under 35 U.S.C. 154(b) by 1002 days.

(21) Appl. No.: 11/428,916

(22) Filed: Jul. 6, 2006

(65) Prior Publication Data
US 2008/0094773 A1 Apr. 24, 2008

(51) Int. Cl.
*H05F 3/04* (2006.01)
(52) U.S. Cl. .................................. 361/119
(58) Field of Classification Search ............ 361/112, 361/119; 428/329
See application file for complete search history.

(56) References Cited

U.S. PATENT DOCUMENTS

| 4,726,991 A * | 2/1988 | Hyatt et al. ............ 428/329 |
| 6,999,294 B2 * | 2/2006 | Festag et al. ............ 361/112 |

* cited by examiner

*Primary Examiner*—Stephen W Jackson
*Assistant Examiner*—Angela Brooks
(74) *Attorney, Agent, or Firm*—Miles & Stockbridge P.C.

(57) ABSTRACT

Electrostatic discharge protection for guided wave microwave structures is provided by a protection device that imposes minimal disruption on the microwave structures and negligible interference with the normal operation of the structures. The protection device provides a discharge path between a signal conductor and a ground conductor when electrostatic charges on the signal conductor reach a predetermined voltage level. The protection device includes an insulating base that bridges a space between the signal conductor and the ground conductor and that supports a dispersion of metal particles adhered to the base.

19 Claims, 3 Drawing Sheets

ELECTROSTATIC DISCHARGE PROTECTION FOR MICROWAVE GUIDED WAVE STRUCTURE

CROSS-REFERENCE TO RELATED APPLICATION

This application claims the benefit of Provisional application Ser. No. 10/699,222 filed Jul. 13, 2005, incorporated herein by reference.

BACKGROUND OF THE INVENTION

This invention is concerned with electrostatic discharge protection for microwave structures and circuits, more particularly, with devices and methods that provide electrostatic discharge protection with minimal disruption and interference with the structure and operation of microwave guided wave structures.

Electrostatic discharge protection devices for electronic systems operating at frequencies below 1 GHz are well known. More recently, there has been a need for providing electrostatic discharge protection in higher frequency (microwave) structures and circuits that operate above 1 GHz (e.g., between 1 GHz and 20 GHz). Waveguide structures operating in the microwave regime include microstrip, stripline, and coplanar guide structures, for example. Prior protection devices, such as zener diodes and variable resistors, have a rather large capacitance that interferes with the desired operation of microwave structures and circuits. The large capacitance and the inductance of the packaging leads create a self resonance that limits the utility of such devices above 1 GHz. Moreover, the packaging and mounting of the prior art protection devices further limit their use.

Any electrostatic discharge device should provide minimum disruption or loading of the circuits with which they are used. Furthermore, when the voltage levels associated with the build up of electrostatic charges reach a threshold level, the devices should act quickly to present a low impedance path for electrostatic discharge. Once the voltage threshold is reached (typically 100-2000 volts), the electrostatic discharge should lower the voltage by a factor of 50% or more by rapidly and fully conducting excess charge to ground.

Prior to the present invention, there have been no effective and practical electrostatic discharge devices for use in microwave structures and circuits.

BRIEF DESCRIPTION OF THE INVENTION

The present invention provides an effective and practical solution to the problem of electrostatic discharge protection for microwave structures and circuits of the coplanar, microstrip, and stripline type, for example. The invention utilizes a protection device that can be added to existing guided wave structures (or during manufacture of such structures) with minimal disruption of the structures and with minimal interference with their normal operation. In a preferred form, a protection device of the invention includes an insulating base that bridges a space between a signal conductor and a ground conductor (e.g., ground plane) or a space between a signal conductor and a conductive member that extends from the ground conductor. The insulating base of the protection device supports a structure that provides an electrostatic discharge path for discharging electrostatic charges that build up on the signal conductor to a predetermined voltage level. More particularly, an electrostatic discharge protection device of the invention uses an insulating material (e.g., polyester) applied as a liquid film that sets, and onto which a plurality of metal particles are dispersed before the film sets, so that the particles adhere to the film.

BRIEF DESCRIPTION OF THE DRAWINGS

The invention will be further described in conjunction with the accompanying drawings, which illustrate preferred (best mode) and exemplary embodiments of the invention, and wherein.

DETAILED DESCRIPTION OF THE INVENTION

Figure 1:
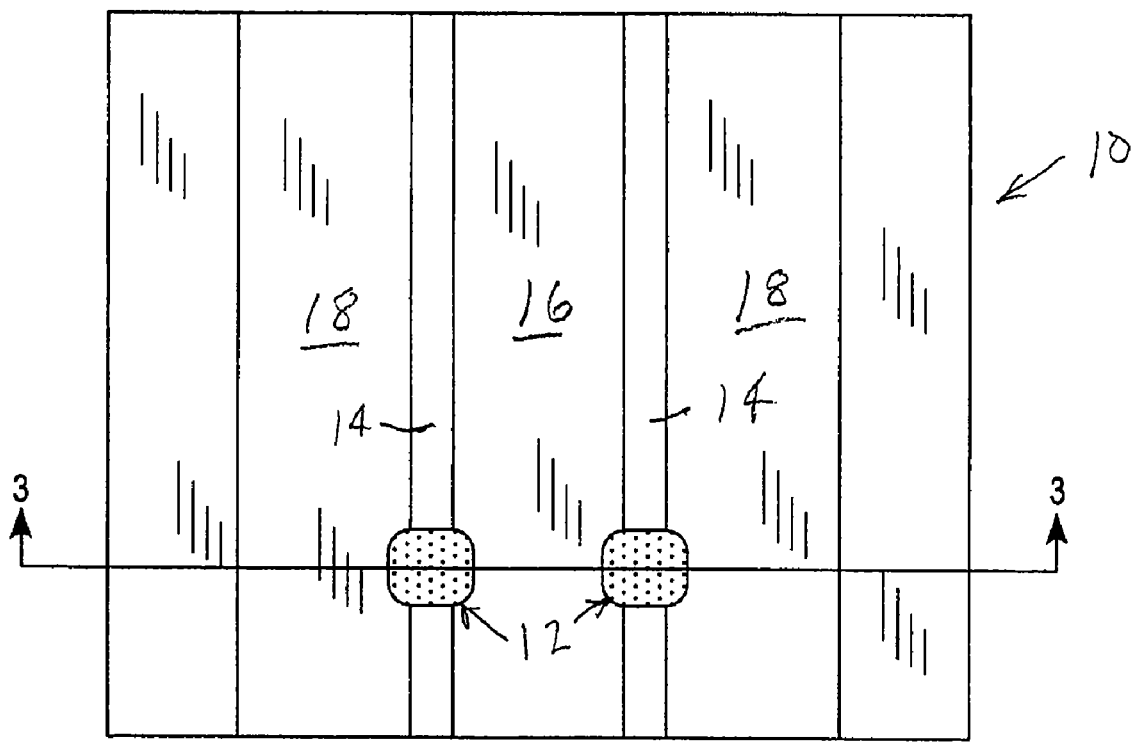
FIG. 1 is a plan view showing the use of electrostatic discharge protection devices of the invention in a coplanar type microwave structure.
Figure 2:
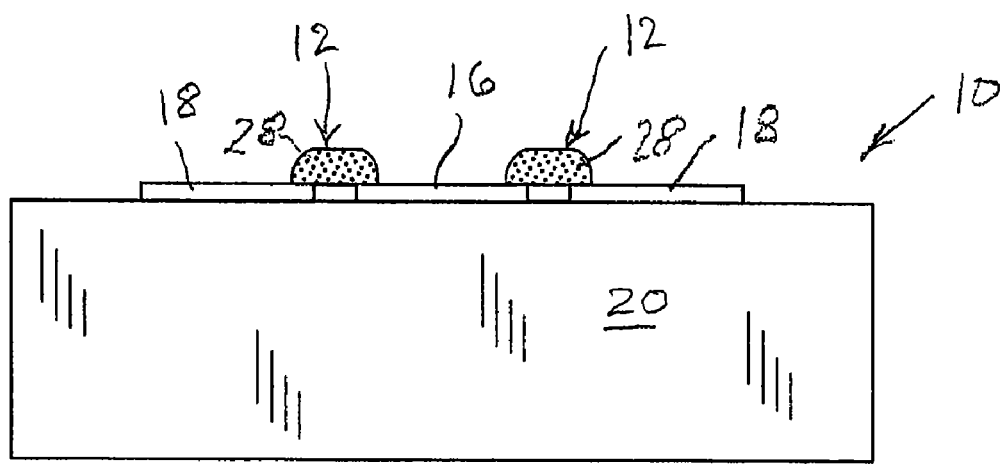
FIG. 2 is an end elevation view of the embodiment of FIG. 1.
Figure 3:
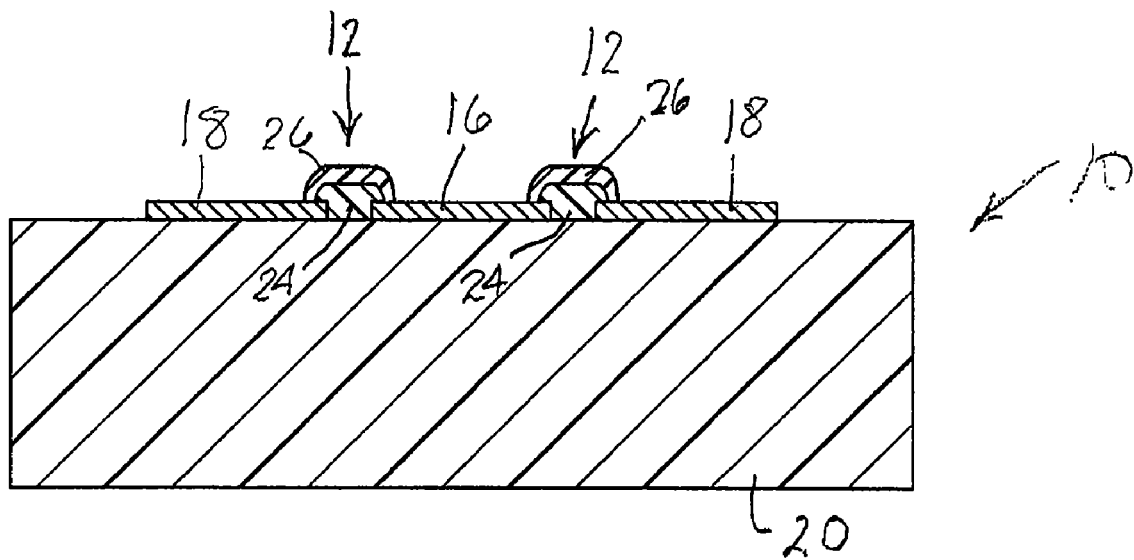
FIG. 3 is a cross-sectional view taken along the line 3-3 in FIG. 1.

The invention will first be described in its application to electrostatic discharge protection of a coplanar type microwave structure 10, shown in FIGS. 1-3. In this embodiment, there are two electrostatic discharge protection devices 12 that bridge spaces 14 between a signal conductor 16 and a pair of ground conductors 18 at opposite edges of the signal conductor, all being supported by a dielectric 20. The construction of the coplanar microwave structure (as well as others to be described hereinafter) is conventional and need not be described in detail.

Each electrostatic discharge protection device has a body that includes an insulating base supporting a structure that provides an electrostatic discharge path for discharging electrostatic charges that build up on the signal conductor to a predetermined voltage level. In a preferred form, the base comprises two layers of insulation, a first of which 24 is adhered to the structure to be protected and the second of which 26 is adhered to the first layer and supports a plurality of conductive particles 28.

In the preferred embodiment, the electrostatic discharge protection device of the invention is formed by applying, across a space between a signal conductor and a ground conductor, a liquid film of polyester material that is allowed to set. Then a second film of polyester material is applied to the first film. Before the second film sets, metal particles, preferably brass filings (or other suitable conductive particles), are sprinkled onto the second film and become at least partially embedded in the second film so that they adhere thereto when the second film sets. The dispersion of metal particles is a thin layer that provides a myriad of gaps between metal particles, many of which are exposed to a surrounding gaseous environment, such as the air atmosphere. The particles are preferably multi-faceted and multi-pointed.

The electrostatic discharge device of the invention imposes minimal disruption to a guided wave structure, and interference with the normal operation of the structure is negligible. When an electrostatic voltage build-up on a signal conductor reaches a predetermined threshold level due to the accumulation of electrostatic charges, the protection device of the invention provides an electrostatic discharge path between the signal conductor and a ground conductor. Once the voltage threshold is reached (typically 100-2000 volts), a low impedance discharge path is provided very quickly (e.g., in less than 0.3-60 nS), to lower the built-up voltage by a factor of 50% or more.

The voltage threshold is controlled by a combination of the spacing of the metal particles and the surrounding gaseous environment. The nature and pressure of the gaseous environment can be controlled by enclosing the protection device and a portion of the protected structure in a controlled environment.

When an electrostatic discharge occurs in the use of the invention, a spark can often be seen, and black traces can be seen on the exposed surface of the protection device. These effects do not appear to inhibit future operation of the device in the intended manner. While different hypotheses can be offered for the manner in which the invention functions, one is that the electrostatic discharge involves ionization of the gaseous medium in contact with the protection device, and the production of secondary electrons (electron multiplication). It is preferred that the material of the metal particles have a secondary electron coefficient greater than 1, to promote an avalanche of electron flow, once the voltage threshold is met.

In one embodiment of the invention, the insulation material used to form the base of the protection device was provided as a liquid that has a modest viscosity, and that dries quickly without the addition of heat. More particularly, the insulation material used was Revlon #771 clear fingernail polish that includes the following ingredients:

Butyl Acetate
Ethyl Acetate
Nitro-cellouse
Glycerol Tribenzoate
Arcylates copolymer
Isopropyl Alcohol
Glycerol Triacetate
Polyester/Urethane polymer
SD alcohol
Dimenthecone.

The polyester ingredient is believed to provide the basic desired insulating material.

To produce a protection device in one embodiment of the invention, a thin film of nail polish was applied at a small region of the structure to be protected, to bridge the space between a signal conductor and a ground conductor, and was allowed to dry. Then a second film was applied in a similar manner. Before the second film was permitted to dry (set), brass particles was sprinkled onto the second film to produce a dispersion of particles that adhered to the second film. After the second film was permitted to dry, air was blown over the second film to remove any metal particles that failed to adhere.

The brass particles preferably have a size range within about 10 to about 50 microns. The composite of two thin films may have a thickness within the range of about 50 to about 300 microns, for example, but thinner films are preferred.

Figure 4:
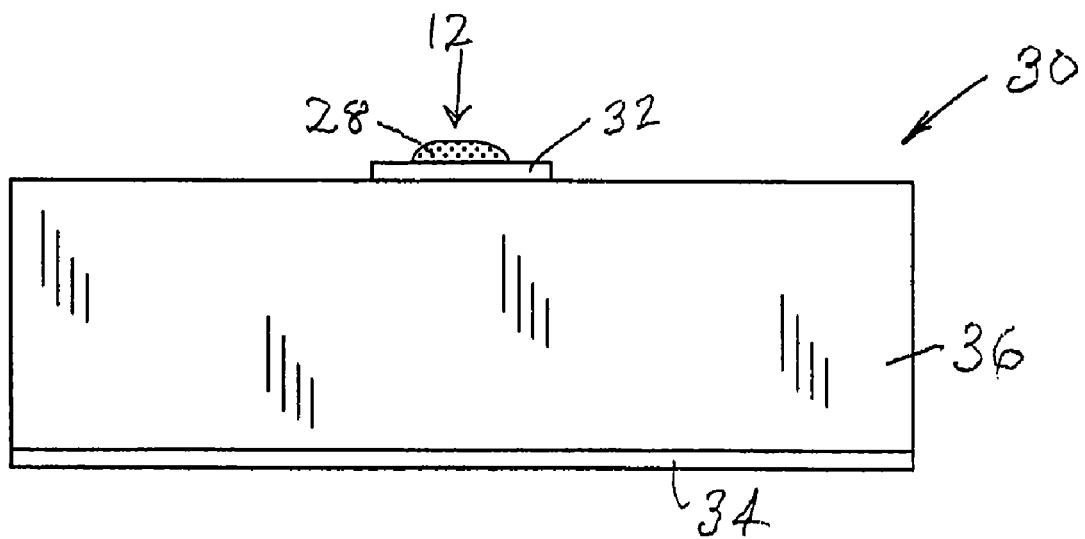
FIG. 4 is an end elevation view showing the use of a protection device of the invention in a microstrip type microwave structure.
Figure 5:
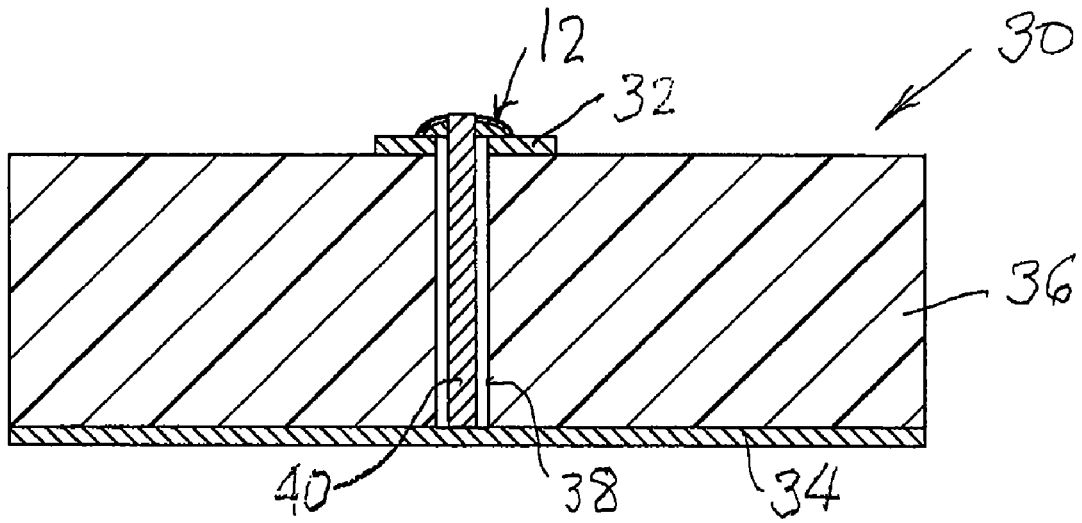
FIG. 5 is a cross-sectional view of the embodiment of FIG. 4.

FIGS. 4 and 5 show an embodiment of the invention applied to a microstrip type of microwave structure 30. As is well known, such a structure comprises a signal conductor 32 and a ground conductor 34 (ground plane) on opposite sides of a dielectric 36. To facilitate the provision of a protection device of the invention, a hole 38 (via) is bored through the center of the signal conductor and through the dielectric to the ground plane. A conductive post 40 is inserted centrally in the hole, spaced from the sidewall of the hole, and is mounted in the hole with one end of the post in electrical contact with the ground plane and the opposite end of the post protruding through the signal conductor. The hole may have a diameter of 1.2 mm, for example, and the post may have a diameter of 1 mm, leaving an annulus gap of about 0.1 mm between the post and the signal conductor. A protection device 12 of the invention is then formed, in the manner described above, so that it bridges the space between the post and the signal conductor.

Figure 6:
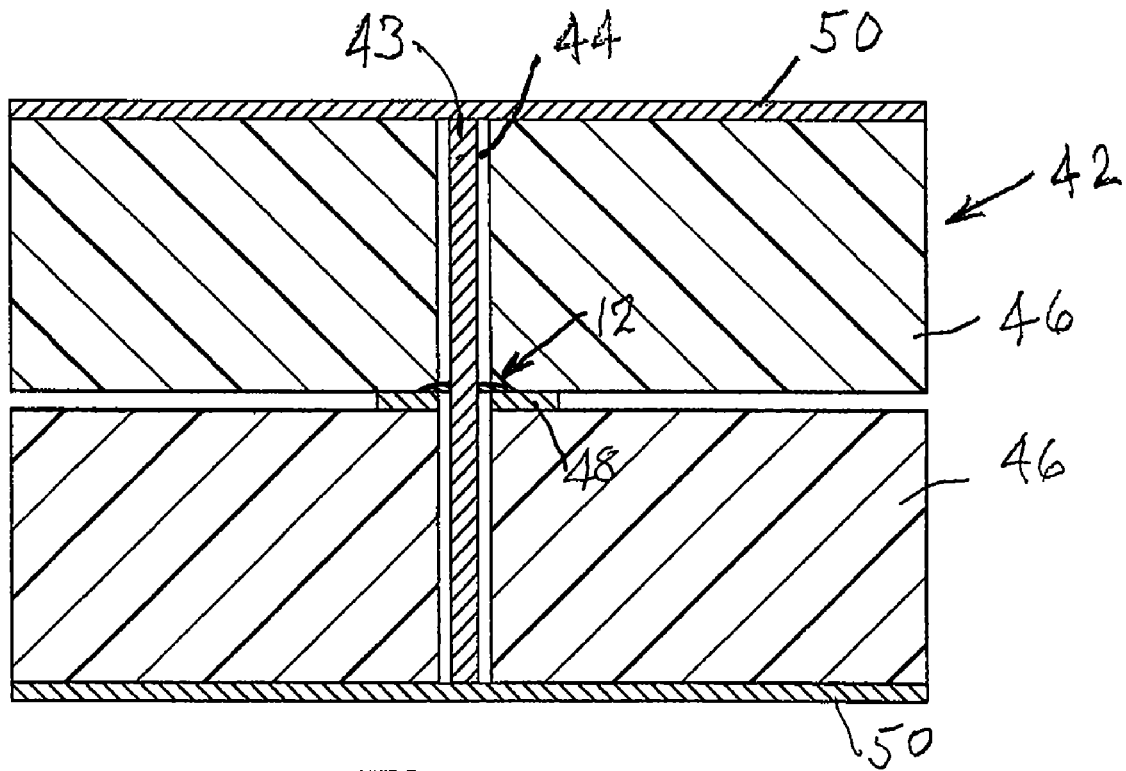
FIG. 6 is a cross-sectional view showing the use of a protection device of the invention in a stripline type of microwave structure.

FIG. 6 shows an embodiment of the invention applied to a stripline microwave structure 42. To implement this embodiment a conductive post 43 is provided in a hole 44 through the dielectric 46 and the signal conductor 48 and is in electrical contact with the ground planes 50 but electrically isolated from the signal conductor. A protection device 12 of the invention is then formed so as to bridge the space between the post and the signal conductor in the manner described with respect to the previous embodiment. The foregoing can be accomplished during the manufacture of the stripline microwave structure when the internal parts are exposed and accessible. The conductive post need not contact both ground planes, contact with one ground plane being sufficient.

The invention preferably makes use of a symmetrical construction. For example, in coplanar microwave structures two protection devices of the invention are provided at opposite edges of the signal conductor. In microstrip and stripline microwave structures the invention is applied at a central region of the signal conductor. In those structures, the invention takes advantage of the fact that as the signal frequency increases, the charge density becomes greater along the edges of the signal conductor.

While preferred embodiments of the invention have been shown and described, changes can be made without departing from the principles and spirit of the invention, the scope of which is defined in the accompanying claims. For example, there may be advantages in subjecting the protection devices of the invention to selected gaseous environments (e.g., helium) during formation of the protection devices (and/or during their operation), using pressures below or above normal atmospheric pressure. Also, while the protection devices of the invention are disclosed as incorporated in guided wave structures to be protected, it will be understood that the protection devices can be provided as separate units to be connected to guided wave structures to be protected.

What is claimed is:

1. An electrostatic discharge protection device for a guided wave structure operating in the microwave frequency regime, comprising a body constructed to be interposed between a signal conductor and a ground conductor of the guided wave structure in a manner that interferes negligibly with the operation of the guided wave structure and that provides an electrostatic discharge path between the signal conductor and the ground conductor when a buildup of electrostatic charge on the signal conductor reaches a predetermined level, wherein the body includes an insulating layer to bridge a space between the signal conductor and the ground conductor and a plurality of conductive particles dispersed as a layer on a surface of the insulating layer and exposed to a gaseous environment.

2. The device of claim 1, wherein the conductive particles are brass particles at least partially embedded in the insulating layer.

3. The device of claim 2, wherein the device is incorporated into the guided wave structure.

4. The device of claim 3, wherein the insulating layer is part of an insulating base that bridges a space between the signal conductor and the ground conductor.

5. The device of claim 4, wherein the guided wave structure is a coplanar type that has a central signal conductor and a pair of ground conductors spaced from opposite edges of the signal conductor in a coplanar arrangement on a dielectric, and wherein there are a pair of the devices bridging respective spaces between the signal conductor and the ground conductors.

6. The device of claim 1, wherein the conductive particles have a secondary electron coefficient greater than 1.

7. The device of claim 1, wherein the insulating layer comprises polyester.

8. The device of claim 1, wherein the insulating layer comprises films with composite thickness in the range of about 50 microns to about 300 microns.

9. The device of claim 1, wherein the conductive particles have a size within the range of about 10 microns to about 50 microns.

10. The device of claim 9, wherein the conductive particles are brass.

11. The device of claim 1, wherein the gaseous environment is air.

12. The device of claim 1, wherein the gaseous environment is contained.

13. An electrostatic discharge protection device for a guided wave structure operating in the microwave frequency regime, comprising a body constructed to be interposed between a signal conductor and a ground conductor of the guided wave structure in a manner that interferes negligibly with the operation of the guided wave structure and that provides an electrostatic discharge path between the signal conductor and the ground conductor when a buildup of electrostatic charge on the signal conductor reaches a predetermined level,
wherein the body includes an insulating layer to bridge a space between the signal conductor and the ground conductor and a plurality of conductive particles dispersed on the insulating layer,
wherein the conductive particles are brass particles at least partially embedded in the insulating layer,
wherein the device is incorporated into the guided wave structure,
wherein the insulating layer is part of an insulating base that bridges a space between the signal conductor and the ground conductor,
wherein the guided wave structure is a microstrip type that has a signal conductor and a ground conductor at opposite sides of a dielectric, wherein a conductive post extends from the ground conductor through the dielectric and through an opening in the signal conductor, spaced from the signal conductor, and wherein the protection device bridges a space between the post and the signal conductor.

14. An electrostatic discharge protection device for a guided wave structure operating in the microwave frequency regime, comprising a body constructed to be interposed between a signal conductor and a ground conductor of the guided wave structure in a manner that interferes negligibly with the operation of the guided wave structure and that provides an electrostatic discharge path between the signal conductor and the ground conductor when a buildup of electrostatic charge on the signal conductor reaches a predetermined level,
wherein the body includes an insulating layer to bridge a space between the signal conductor and the ground conductor and a plurality of conductive particles dispersed on the insulating layer,
wherein the conductive particles are brass particles at least partially embedded in the insulating layer,
wherein the device is incorporated into the guided wave structure,
wherein the insulating layer is part of an insulating base that bridges a space between the signal conductor and the ground conductor,
wherein the guided wave structure is a stripline type that has a signal conductor centrally located between adjacent sides of two dielectrics, opposite sides of which have ground conductors thereon, wherein a conductive post extends between at least one of the ground conductors through at least one of the dielectrics and through an opening in the signal conductor, spaced from the signal conductor, and wherein the device bridges a space between the conductive post and the signal conductor.

15. A method of providing an electrostatic discharge device that bridges a space between a signal conductor and a ground conductor, comprising:
applying an insulating base between the conductors; and
forming on said insulating base a structure that provides a conductive path between the signal conductor and the ground conductor when electrostatic charges on the signal conductor reach a predetermined level, wherein the structure formed on the base comprises a dispersion of conductive particles formed as a layer on a surface of the insulating base and exposed to a gaseous environment.

16. The method of claim 15, wherein the particles are brass particles.

17. The method of claim 15, wherein the particles are at least partially embedded in the base.

18. The method of claim 15, wherein the base includes a liquid film that sets, and wherein the particles are applied to the film before it sets.

19. The method of claim 15, wherein the base includes a polyester film that sets after being applied as a liquid, and the particles are brass particles applied to the film before it sets.

* * * * *